United States Patent [19]

Kambin

[11] Patent Number: 4,844,088
[45] Date of Patent: Jul. 4, 1989

[54] SURGICAL CUTTING DEVICE WITH RECIPROCATING CUTTING MEMBER

[76] Inventor: Parviz Kambin, 2027 Pine St., Philadelphia, Pa. 19103

[21] Appl. No.: 131,879

[22] Filed: Dec. 11, 1987

[51] Int. Cl.⁴ ............................................. A61B 10/00
[52] U.S. Cl. .................................................... 128/753
[58] Field of Search ............................... 128/750–754, 128/305; 604/22, 43, 173

[56] References Cited

U.S. PATENT DOCUMENTS

| | | | |
|---|---|---|---|
| 3,605,721 | 9/1971 | Hallac | 128/754 |
| 3,606,878 | 9/1971 | Kellogg | 128/753 |
| 3,732,858 | 5/1973 | Banko | 128/753 |
| 4,203,444 | 5/1980 | Bonnell et al. | 128/752 |
| 4,662,869 | 5/1987 | Wright | 128/752 |
| 4,681,123 | 7/1987 | Valtctev | 128/753 |

FOREIGN PATENT DOCUMENTS 1161400  3/1958  France ................. 128/753

*Primary Examiner*—Max Hindenburg
*Attorney, Agent, or Firm*—Caesar, Rivise, Bernstein, Cohen & Pokotilow, Ltd.

[57] ABSTRACT

A surgical cutting device, particularly suited for back surgery where a ruptured disk is involved. The device includes an elongated, narrow tube which has a smooth end for insertion into the area adjacent the required surgery. The tube further includes at least a single opening on the lateral surface of the tube adjacent the smooth end. The opening extends into the bore of the tube, with the bore extending substantially the length of the tube. The device further includes a cutting member having a periphery which is embraced and is slidable within the bore of the tube. The cutting member is reciprocally slidable within the tube so that the forwardmost surface of the cutting member traverses the opening to enable cutting of any material that is located in the opening and suction means connected to the bore of the tube for drawing loose materials to the side of the opening for cutting. The cutting member has an opening which extends longitudinally through the member to enable the vacuum caused by the suction means to communicate with the opening. The surgical device also includes means for providing fluids through the opening to further facilitate removal of loose tissue.

1 Claim, 3 Drawing Sheets

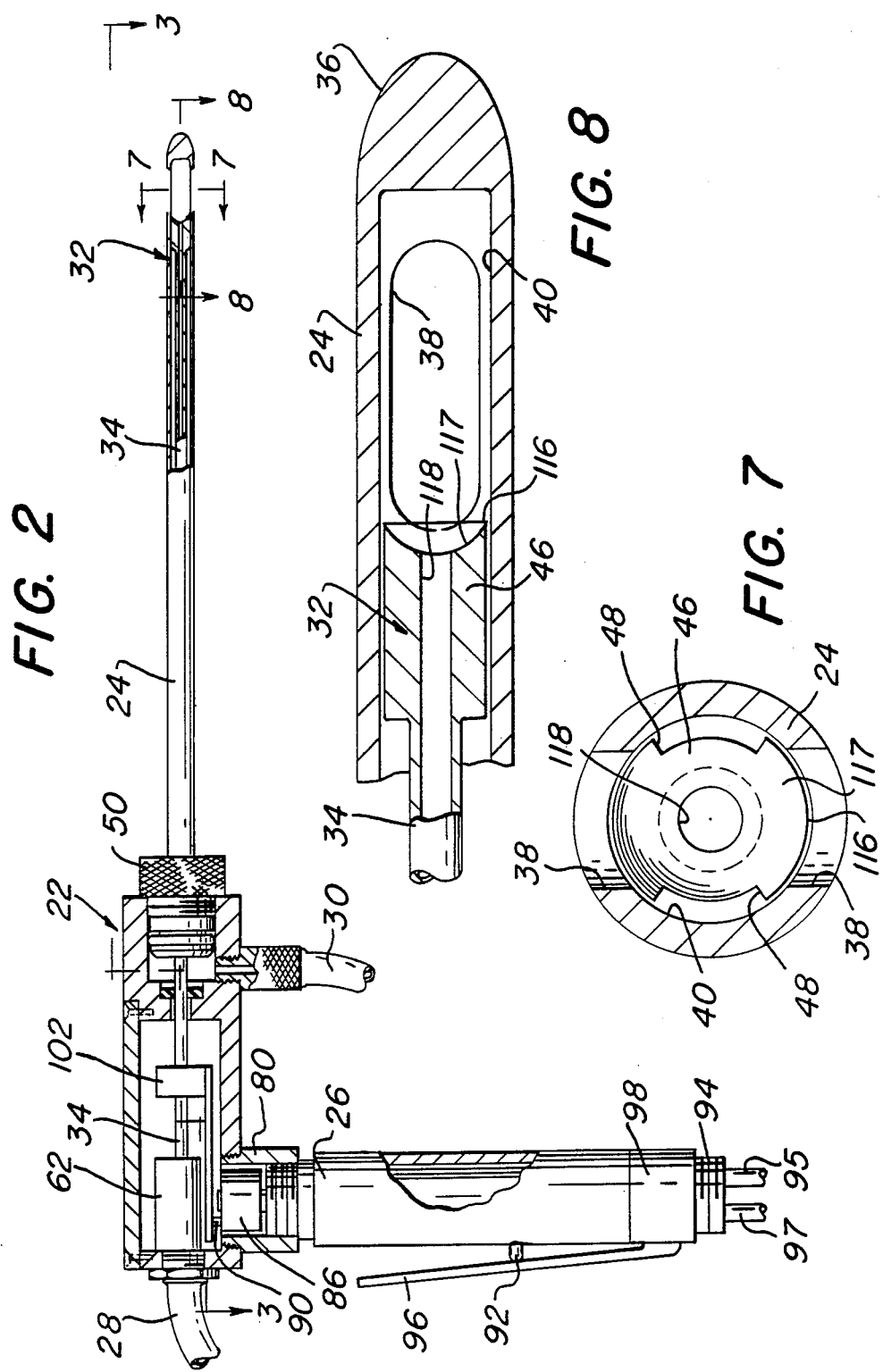

SURGICAL CUTTING DEVICE WITH RECIPROCATING CUTTING MEMBER

BACKGROUND OF THE INVENTION

This invention relates generally to surgical devices and more particularly to a surgical device for back operations.

Lower back surgery where a ruptured disk is involved has historically been a debilitating operation to a patient because the patient's back had to be opened up and the back muscles had to be cut so that the surgeon could see what he was doing. Accordingly, the consequence of such an operation was that a patient had to stay in a hospital for typically ten days even where the operation was successful in removing the ruptured portion of a disk.

Recent innovations in arthroscopic surgery have led to the use of tube techniques in back operations.

Where surgery is used for the removal and repair of tissue near the lower back, the only access to the area requiring removal that is available for the surgeon is the path used for the cutting instrument itself which is inserted into the back. That is, the opening must be small to avoid having to cut muscles in order to cut away the ruptured disk from the vertabrae.

In order for a surgeon to remove a ruptured portion of a disk the patient must be rested on his stomach, held in a stationary position, and only a local anesthetic used. See, for example, my U.S. Pat. No. 4,573,448 issued on Mar. 4, 1986. The patient is kept awake in order to prevent inadvertent injury to nerves. The surgeon counts the vertebrae to determine the exact position of the area in which the ruptured disk is located, and then a needle is inserted in order to find the ruptured disk.

After the needle is inserted, the C-arm of an X-ray unit is positioned in two different positions for taking X-rays of the location of the needle with respect to the vertabrae. When it is determined from the X-ray images that the needle is in the correct position with respect to the vertebrae, the stylet of the needle is replaced by a wire, the surgeon slides a probe over the wire, and inserts it into the same position at which the needle was located. By sequentially inserting a larger tube which is approximately five millimeters in diameter, the probe is then removed and there is then an orifice that is achieved which goes directly to the vertabrae at the location where the ruptured disk is attached, which orifice is approximately five millimeters in diameter.

A long narrow scissor device can then be placed through the narrow orifice to cut away from the vertebrae the ruptured portion of the disk. When the ruptured portion of the disk is cut away from the vertebrae, the loose portions of the disk can then be cut away from the disk. A problem that remains with this arthroscopic-like surgery is the need for accurate and efficient removal of the portion of the disk which has been ruptured and which has been cut away from the vertebrae and other loose tissue in the area, which problem is created by the fact that the surgeon cannot see the tissue being removed.

X-ray photographs must continually be taken during the surgery in order to determine the location of the cutting tool with respect to the vertebrae. The condition of the patient must also be monitored to determine that the cutting tools used to cut away and remove the ruptured disk are not impinging on any nerves of the patient.

Accordingly, a quick-acting tool has been required by surgeons which will not create a dangerous situation for the patient and cut away a nerve and also which will effectively and efficiently and accurately remove the ruptured portion of the disk and loose tissue in the area.

Thus, the need exists for a surgical instrument which facilitates insertion into the patient's back through an extremely small opening of the magnitude of approximately five millimeters which facilitates cutting away and removing all loose materials in the area where the ruptured disk has been cut away from the vertebrae.

OBJECTS OF THE INVENTION

It is a general object of this invention to provide a surgical instrument for use in a back operation which efficiently and quickly removes the ruptured portion of a disk in the location where the vertebrae has been cut away from the disk.

It is a further object of this invention to provide a surgical device for effectively cutting away and removing the tissue in surgical applications affording limited access to the surgical situs, particularly in back surgery.

It is a further object of this invention to provide a surgical device which is simple in construction, effective in operation and cost effective.

It is an other object of this invention to provide a surgical instrument having a cutting tool which quickly cuts away materials which are loosely floating in the general area of the vertebrae adjacent the disk without the risk of cutting any nerves in the area and without excess damage of surrounding tissue during the insertion process.

It is a further object of this invention to provide a surgical device which has particular utility for back operations and efficient removal of cut-away portions of a ruptured disk.

SUMMARY OF THE INVENTION

These and other objects of the instant invention are achieved by providing a surgical cutting device which is used for cutting and removing loose material in the area of the vertebrae adjacent the ruptured disk. The device comprises an elongated and narrow tube which has a smooth tapered end for insertion into the area adjacent the required cutting. The tube further includes at least a single opening on the lateral surface of the tube adjacent the smooth end. The opening extends into the bore of the tube. The bore extends substantially the length of the tube. The cutting device further includes a cutting member having a periphery which is embraced and is slidable within the bore of said tube. The cutting member is reciprocally slidable within the tube so that the forwardmost surface of the cutting member traverses the opening to enable cutting of any material that is located in the opening and suction means connected to the bore of the tube for drawing the loose materials in side of the opening for cutting. The cutting member has an opening which extends longitudinally through the member to enable the vacuum caused by the suction means to communicate with the opening. A source of fluid is also provided to enable fluid to be ejected through the cutting member to facilitate removal of the loose materials.

DESCRIPTION OF THE DRAWINGS

Other objects and many of the attendant advantages of the instant invention will be readily appreciated as the same becomes better understood by reference to the following detailed description when considered in connection with the accompanying drawing wherein:

FIG. 2 is an enlarged vertical sectional view taken along the line 2—2 of FIG. 1 with certain portions shown in full for purposes of clarity;

FIG. 7 is an enlarged sectional view taken along the line 7—7 of FIG. 2; and

FIG. 8 is an enlarged sectional view taken along the line 8—8 of FIG. 2.

DETAILED DESCRIPTION OF THE PREFERRED EMBODIMENT

Figure 1:
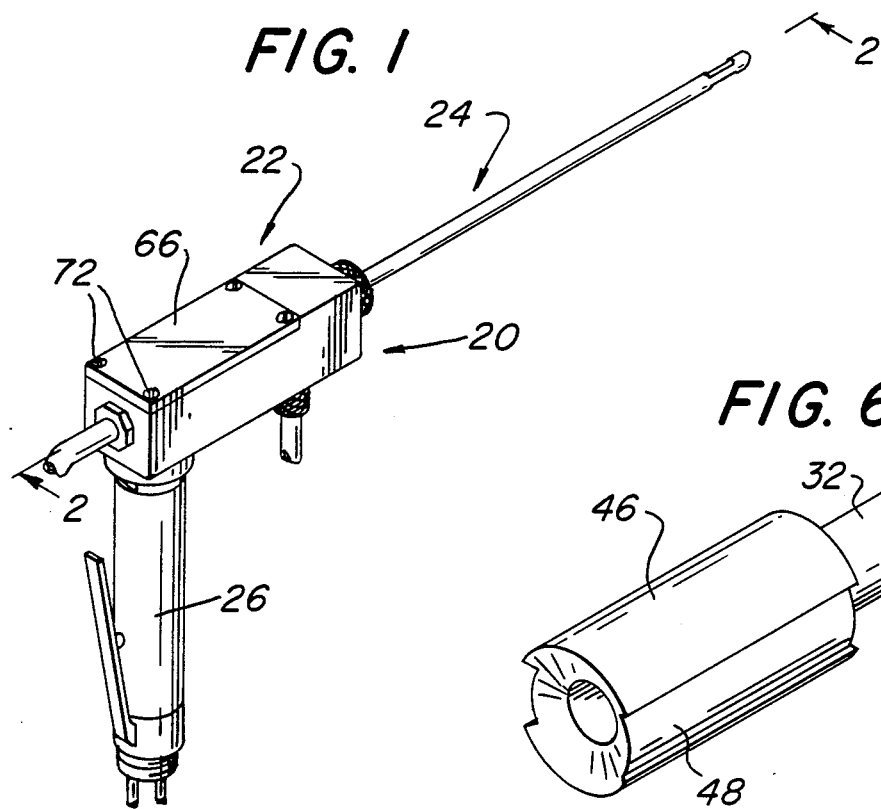
FIG. 1 is a perspective view of a surgical device for back operations constructed in accordance with this invention.
Figure 6:
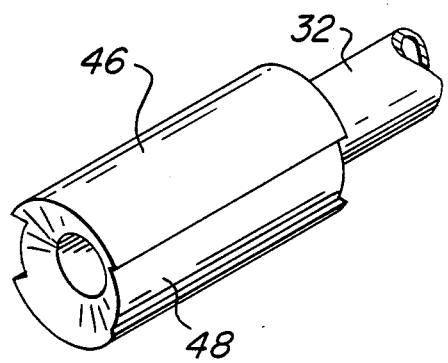
FIG. 6 is an enlarged sectional view of the cutting member used in the surgical device.

Referring now in greater detail to the various figures of the drawing wherein like reference characters refer to like parts, there is shown at 20 in FIG. 1 a surgical device for back operations.

The surgical device 20 basically comprises a body portion mounted within housing 22, and a probe portion which includes an elongated tube 24, which contains the cutting member, and a handle 26 which contains a pneumatic motor for powering the cutting member disposed in tube 24.

As best seen in FIG. 2, the housing 22 has connected thereto a suction tube 28 which is connected to a source of a reduced atmospheric pressure and a tube 30 which provides a supply of fluid to the housing. Within tube 24 is provided a cutting member 32 which, as best seen in FIG. 8, is connected by an elongated tubular stem 34 to a motor to provide a reciprocating driving of the cutting member 32 so that it is moved back and forth within tube 24. As best seen in FIG. 8, tube 24 includes a smooth convex tapered end 36 and has, adjacent to the end 36 on the lateral surface on opposing sides a pair of elongated openings 38. The openings 38 extend from the outer surface of the tube 24 into the bore 40 of the tube 24. The bore of tube 40 extends substantially the length of the tube 24 from the end 36 to the housing 22.

The cutting member 32 includes an enlarged cylindrical head 46 which is best seen in FIGS. 7 and 8. The outside periphery of the cylindrical head 46 is essentially the diameter of but slightly smaller than the diameter of the bore 40 of tube 24. The cylindrical head 46 is thus embraced and slidably mounted within the elongated bore 40 so that it can move back and forth past the openings 38 in the tube 24.

The cylindrical portion 46 of the cutting head also includes a pair of grooves 48 which, as will hereinafter be seen in greater detail, permits fluid to be ejected through the grooves 48 and out opening 38 into the area where the cutting and suction enables the removal of the loose materials adjacent the vertebrae. The grooves 48 are each aligned with the portion of bore 40 which is not in line with openings 30. That is, the back and forth reciprocating movement of cutting head 46 does not take the grooves 48 past openings 38.

Figure 4:
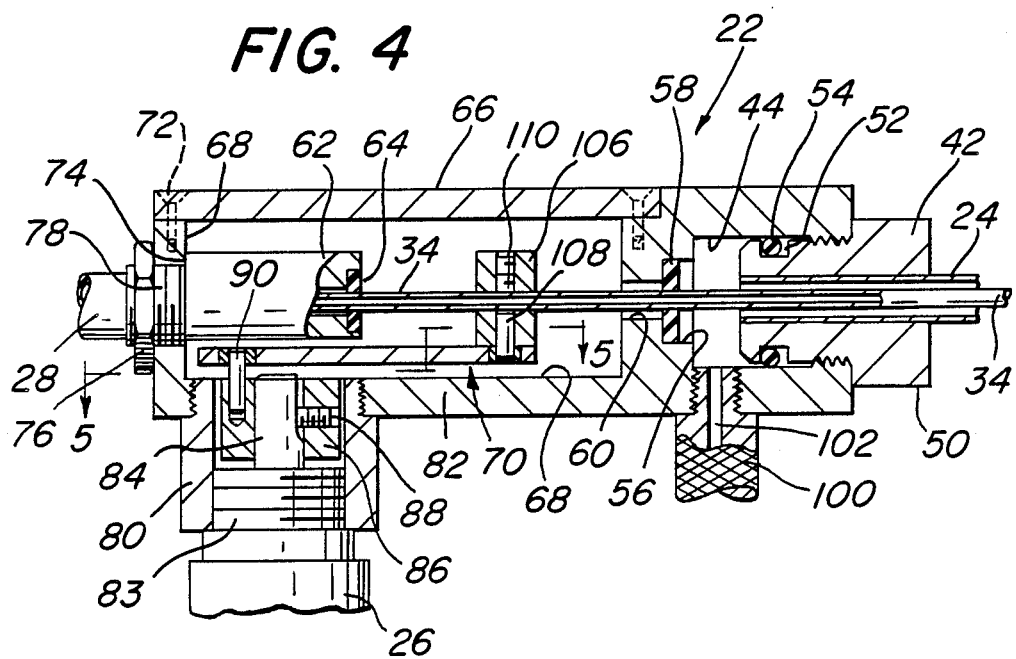
FIG. 4 is a further enlarged vertical sectional view of the body portion of the surgical device shown in FIG. 2.

As seen in FIGS. 2 and 4, the threaded securement member 42 includes a knurled surface 50 which permits the manual rotation of the threaded securement member 42 into threaded securement within the cylindrical opening 44 in housing 22. In front of the threaded portion of securement member 42 there is provided a smooth portion with an annular groove 52 in which an 0-ring 54 is provided.

The cylindrical opening 44 includes a reduced section 56 in which a sealing ring 58 is provided. The sealing ring 58 is press fit in place against the wall separating the reduced portion 56 of opening 44 from the smallest portion 60 of the cylindrical opening 44.

As can best be seen in FIG. 4 the tubular stem 34 of the cutting member extends not only through the tube 24, but extends into opening 44 past the reduced portions 56 and 60 and extends to a cylindrical housing 62 within the overall housing 22. At the entrance of housing 62 is a sealing ring 64 which is press fit into a cylindrical opening at the end of the housing 62. The sealing ring 64 permits movement of the stem 34 back and forth within the housing 62 while maintaining a substantially airtight seal about the periphery of stem 34.

Housing 22 includes a removable rectangular plate 66 which is secured by fasteners to the remaining portion of the rectangular housing 22. A rectangular bore 68 is provided within housing 22 in which housing 62 is disposed along with the linkage 70 which converts the rotational movement of the output shaft of the motor provided in the handle housing 26 to a linear back and forth movement of the cutting member 32.

The plate 66, as best seen in FIG. 4, is releasably secured by threaded securement members 72 to permit access to the bore 68 of the housing. At the end wall 74 of the housing, the cylindrical housing 62 is secured by a nut 76 which is threadedly secured to a threaded boss 78 which is integral of housing 62. The boss 78 extends through a cylindrical opening in the housing provided therefor and the housing 62 is secured against the end wall 74 of the housing 22.

The interior of housing 62 is in communication with the flexible tube 28 which is connected to a source of a partial vacuum. There is thus a gas passage from the source of the partial vacuum through tube 28, housing 62 and via stem 34 through cutting head 46 and openings 38 out the tube 24.

In the bottom wall 82 of the housing 22 there is provided a securement member 80 which is threadedly secured in an opening in bottom wall 82 of the housing 22. The handle housing 26 is threadedly secured by a threaded boss within the securement member 80 which has a threaded hollow bore through which the stem 84 of the motor extends.

An annular ferrule 86 is connected to the stem 84 and has a threaded opening which extends transversely to the axis of the shaft in which a threaded fastener 88 is provided for securing the member 86 in a stationary position with respect to the shaft 84. The ferrule 86 includes a pin 90 which extends parallel to and is radially spaced from the shaft 84 of the motor, which pin 90 is press fit into an opening on the end of ferrule 86. The pneumatic motor which is of conventional construction and is not shown is provided within the handle housing 26. The motor includes an air valve, also not shown, mounted within the housing 26 at the opposite end of the portion of the handle 26 which is secured to the housing 22.

The air valve includes a valve actuator button 92 (FIG. 2). The valve includes an inlet 94 which is connected to a line 95 carrying pressurized nitrogen. Another line 97 is provided to release the spent nitrogen.

The valve is arranged so that upon the depression of the valve button 92 pressurized nitrogen flows from the air line via the connector into the air motor housed in housing 26. This causes the air motor to operate so that the shaft 84 of the motor rotates.

The depression of the valve button 92 is effected by the surgeon by pressing the actuator arm 96 or squeezing the same so that the button 92 is pressed into the housing. The actuator arm 96 is an elongated lever-like element which is pivotally secured in cylindrical member 98 secured to the handle 26.

With the exemplary motor described above and by the application of nitrogen pressure on the order of 50 psi, the output shaft of the motor rotates at approximately 10,000 rpm, whereby the movement of the cutting member 32 oscillates back and forth at a frequency of 166.67 hertz. By varying the air pressure to the motor, the speed of the motor and hence the frequency of the back and forth oscillation of the cutting member 32 can be controlled as desired by an appropriate amount of pressure applied to the lever arm 96.

Referring back to FIG. 4, it can be seen that there is another orifice into housing 22 provided by a threaded member 100 which is threadedly secured in a threaded opening provided in the housing to provide an opening into cylindrical bore 44. The threaded member 100 includes an elongated bore 102 through which a sterile source of fluid can be inserted into the opening 44. As can be seen, this fluid is provided through the opening between the tubular stem 34 and the bore of tube 24 past the grooves 48 in the cutting head 46 of the cutting member 32, out opening 38 and into the area where the cutting takes place in the patient.

Figure 5:
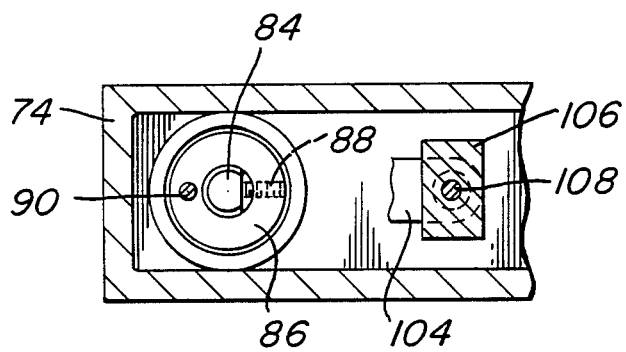
FIG. 5 is an enlarged sectional view taken along the line 5—5 of FIG. 4.

The link and conversion means 70 is best seen in FIGS. 4 and 5. The link and conversion means 70 comprises a linking rod 104, a rectangular securement member 106, pin 108 and the previously mentioned pin 90 which is rotatably secured in ferrule 86.

The rectangular member 106 includes a threaded opening in which a threaded fastener 110 is provided. The opening which contains threaded fastener 110 extends completely through the rectangular member 106 and is in communication and aligned with a cylindrical opening which extends transversely thereto through which the stem 34 extends. This opening in member 106 is slightly larger than the stem 34 so that it can be slid over stem 34 and then the rectangular member 106 is fixed in place with respect to stem 34 by tightening fastener 110 so that it abuts the outer surface of stem 34 thereby fixing the stem in the opening therefor in rectangular member 106.

The pin 108 is provided in the other end of the opening in member 106 by a press fit and extends outwardly thereof so that it extends into an opening provided at one end of the linking rod 104. The pin 108 is journalled in linking rod 104 so that it can be rotated with respect to the linking rod 104. Linking rod 104 also has an opening in which pin 90 extends.

Thus as shaft 34 of the motor in handle 26 rotates, pin 90 is rotated about shaft 84. The rotation of the shaft is thus imparted to the linking rod 104 which causes movement of the rectangular member 106 in a reciprocal path back and forth in the direction of the axis of stem 34 of the cutting member. The stem 34 being slidably disposed in sealing members 64 and 58 thus causes the movement of rectangular member 106 to be fixed along a single line defined by the axis of stem 34. While the linking rod 104 follows at one end pin 90, it causes the pin 108 to move the rectangular member 106 back and forth along the axis of stem 34 and the stem 34 which is fixed with respect to the member 106 is caused to reciprocate along its longitudinal axis slidably confined within sealing members 58 and 64. The stem 34 therefore imparts the reciprocal linear movement to the cutting head 46 which goes back and forth beyond the openings 38 and thereby causes a shearing action with anything that is pulled within the opening 38.

Figure 3:
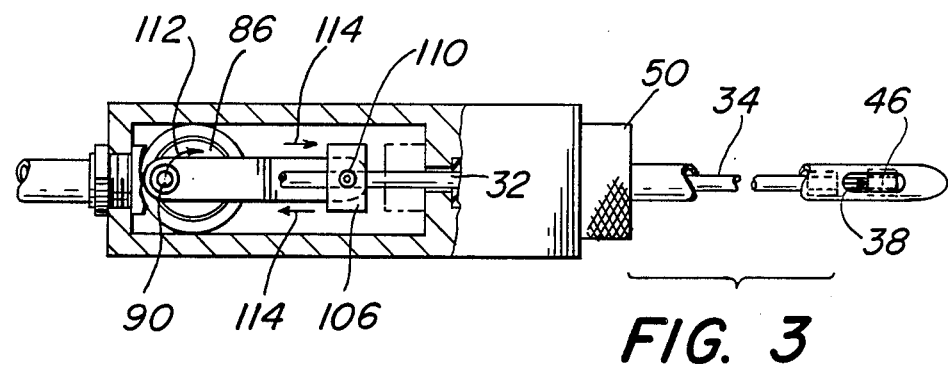
FIG. 3 is a plan and sectional view taken along the line 3—3 in FIG. 2 which is shown with sections removed for purposes of clarity.

Thus, as best seen in FIG. 3, the pin 90 rotates in a clockwise direction as shown by arrow 112 while the rectangular securement member 106 which is secured to the stem 32 is moved in a straight line back and forth in the direction of arrows 114.

Referring to FIG. 8, it can be seen that the cutting head 46 of the cutting member 32 includes a cutting edge 116 at the leading edge of the cutting member 32. The cutting edge 116 is formed by the concave leading surface 117 of the cutting head 46.

Provided in the center of the cutting head 46 and extending through the stem 34 is a bore 118 which, as set forth above, extends all the way to the housing 62. This provides gas communication with tube 28 which extends to the partial vacuum.

Accordingly, as the cutting edge 116 which is provided on the periphery at the leading edge of cutting head 46 of the cutting member cuts loose materials passing into openings 38 of the elongated tube 24, the cut off material is sucked through bore 118 of the cutting member and is pulled out of the body of the patient. The fluid port which is connected to tube 30 is connected to a syringe (not shown) which enables squeezing sterile fluid into the opening in housing 22. The fluid in housing 22 is ejected into the space between the bore 40 of tube 24 and the outer surface of stem 34, through the grooves 48 of the cutting member 46 and into the portion of the bore 40 adjacent openings 38 and out into the patient's body adjacent the ruptured disk. The action of the fluid in combination with the suction member further facilitates sucking out and removal from the body any loose materials and further permits the loose materials to be brought where the cutting action of the cutting member 32 and the inner walls adjacent the openings 38 takes place.

In operation of the surgical device embodying the invention, the surgeon places the patient on a table face down and secures the patient's back in a fixed position on the operating table. The desired position of the vertebrae is located to make an opening into the back by inserting a needle into the body. The needle is positioned adjacent the desired location of the vertebrae and X-ray equipment is then used to visually determine if the correct location of the needle has been accomplished.

When it has been determined by visual observation of the X-ray display that the needle has been placed in the exact position where cutting is required of the ruptured disk from the vertebrae, a tube is inserted. Thus an approximately five millimeter opening is provided through which the tube 24 of the surgical device can be placed.

Prior to the insertion of the tube 24 of the surgical device in the opening, narrow scissor-like instruments are placed through the opening in order to cut away the ruptured portion of the disk from the vertebrae. After the cutting has loosened the ruptured portion from the vertebrae the surgical device is put into operation by inserting tube 24 of the surgical device into the opening adjacent the area where the tissue has been cut loose from the vertebrae.

The suction from the tube 24 which is provided via bore 118 and runs through the entire stem of the cutting member 32 and provides a path via openings 38 into the cutting area, causes the loose tissue to be sucked into the openings 38. Sterile liquid is also emitted by the surgeon through openings 38 into the area to facilitate the loose material being sucked into openings 38.

The lever 96 is then pressed against button 92, thereby opening the valve to the motor and causing rotation of the motor and imparting a reciprocal linear motion of the cutting head 46 past openings 38 thereby causing the cutting of the loose materials so that the materials can be chopped into small enough pieces to be drawn through the bore 118 of the cutting member. Fluid is also provided by the syringe (not shown) through the tube 24, past the grooves 48 in the cutting head 46 and out the openings 38 to facilitate the removal of the tissue that has been cut loose from the vertebrae. When an adequate amount of the disk has been removed, the surgical device can be removed and the incision in the patient is sutured closed. The patient can thus be walking within an hour of the operation. Patients can be permitted to leave the hospital within two days after the operation, because of the small opening that is used for the operation, whereas in the past a ten day hospital stay has been required.

It can therefore be seen that a new and improved surgical device for back operations has been provided. The device permits a very safe removal of loose tissue and eliminates the requirement of opening up a patient and cutting of the muscles surrounding the vertebrae.

The suction enables the tool to remain substantially stationary during cutting and prevents cutting anything other than the tissue desired to be removed. Thus, the operation is quick, safe and healing time is considerably reduced.

It should be noted that the choice of pneumatic power for the instrument is not exclusive. Other types of motors such as electric, hydraulic, etc. can be used.

Without further elaboration the foregoing will so fully illustrate my invention that others may by applying current or future knowledge readily adapt the same for use under various conditions of service.

I claim:

1. A surgical cutting device for cutting and removing loose materials, said device comprising an elongated and narrow tube, said tub having a smooth end for insertion into the area adjacent the required cutting, said tube further including at least one opening on the lateral surface adjacent smooth end, said opening extending into the bore of said tube, said bore extending substantially the length of said tube, said surgical cutting device further including a cutting member having a periphery which is embraced and is slidable within said bore, said cutting member being reciprocally slidable within said tube so that the forwardmost surface of said cutting member traverses said opening to enable cutting of any material that is located in said opening, suction means connected to said bore of said tube for removing loose materials at the site of said cutting, and a source of fluid, said source of fluid having means to enable ejecting said fluid out of said opening to the site where said surgical tool does the cutting, said suction means causing the removal of said fluid and loose materials at the site of said cutting, said cutting device having at least one groove in its periphery which extends in the direction of the length of said tube and provides an opening between the inner wall of said tube and said cutting member as said cutting member moves reciprocally within said tube, said fluid source being connected to the tube at the point forwardmost from the cutting site.

* * * * *